United States Patent [19]

Rosenfeld et al.

[11] Patent Number: 5,120,881
[45] Date of Patent: Jun. 9, 1992

[54] REMOVAL OF NITROGENOUS COMPONENTS OF A HYDROCARBON FEEDSTREAM

[75] Inventors: Daniel D. Rosenfeld; John D. Y. Ou, both of Houston, Tex.

[73] Assignee: Exxon Chemical Patents Inc, Linden, N.J.

[21] Appl. No.: 502,214

[22] Filed: Mar. 30, 1990

Related U.S. Application Data

[63] Continuation-in-part of Ser. No. 274,557, Nov. 22, 1988, abandoned.

[51] Int. Cl.$^5$ .............................................. C07L 41/06
[52] U.S. Cl. .................................. 568/697; 368/699
[58] Field of Search .............................. 568/697, 699

[56] References Cited

U.S. PATENT DOCUMENTS

| | | | |
|---|---|---|---|
| 4,307,254 | 12/1981 | Smith | 568/697 |
| 4,390,413 | 6/1989 | O'Rear et al. | 568/697 |
| 4,465,870 | 8/1984 | Herskovits | 568/697 |

*Primary Examiner*—Howard T. Mars
*Attorney, Agent, or Firm*—Edward F. Sherer

[57] ABSTRACT

A catalytic reaction process which involves exposing a hydrocarbon feed including nitrogenous contaminants as well as dialkyl sulfides to a material capable of adsorbing the nitrogenous contaminants as well as dialkyl sulfides from the feed before introducing the stream substantially devoid of nitrogenous contaminants and dimethyl sulfide into a feed zone of a reactor; contacting the hydrocarbon stream with a catalyst material in the reaction zone; and catalytically reacting the hydrocarbon stream under conditions which favor forming a reaction product and inhibiting reaction of nitrogenous contaminants and dimethyl sulfide with the catalyst material.

12 Claims, 2 Drawing Sheets

REMOVAL OF NITROGENOUS COMPONENTS OF A HYDROCARBON FEEDSTREAM

RELATED APPLICATION

This application is a continuation-in-part application of commonly owned, co-pending U.S. patent Ser. No. 07,274,557 filed Nov. 22, 1988 entitled "Minimizing Deactivation of Ether Synthesis Catalyst", the disclosure of which is hereby incorporated in its entirety by reference thereto.

BACKGROUND OF THE INVENTION

1. Field of the Invention

The present invention relates to methods of conducting catalytic chemical reactions under conditions so as to minimize or substantially avoid deactivation of the catalyst material due to a reaction of polar components, i.e. nitrogenous substances, which may be present in the hydrocarbon feedstream with the catalyst material.

More particularly, the present invention relates to the preparation of alkyl tertiary alkyl ether by catalytic reaction of hydrocarbon streams containing mixtures of isoolefins and alcohols under conditions which minimize or substantially avoid reaction of the catalytic material in the catalytic reaction zone with any nitrogenous components which may be present in the stream.

Specifically, the present invention is directed to a catalytic reaction for producing alkyl tertiary alkyl ether which involves removing nitrogenous components from the hydrocarbon stream prior to introduction of the stream into the catalytic reaction zone to inhibit reaction of the nitrogenous components which may be present in the stream with the catalyst material.

2. Discussion of Background and Material Information

As a general matter, processes are known whereby specific hydrocarbon fractions may be purified using solid adsorbents. In these prior art processes a bed of a solid adsorbent material is contacted with a hydrocarbon stream in either liquid or vapor phase under conditions favorable to adsorption. During contacting, a minor portion of the hydrocarbon stream, including contaminants, is adsorbed into pores in the solid adsorbent, while the major portion, which may be termed the effluent or raffinate, passes through for subsequent processing.

Depending on the process and the product involved, the adsorbent may be used either to adsorb the desired product, which is then desorbed and recovered, or to adsorb the undesired contaminants, to result in an effluent which is the purified product, as is the intended goal of the present invention.

The efficiency of the adsorption is determined by several factors, including the precise adsorbent selected, the contaminants to be adsorbed, temperature, pressure, flow rate of the hydrocarbon stream, and concentrations of feedstream components.

The prior art in this area demonstrates the complexity and the high degree of specificity involved in matching a given feedstock, containing given contaminants, from which a certain product is desired, with a suitable adsorbent under appropriate conditions to arrive at a commercially acceptable process.

U.S. Pat. No. 4,831,206, ZARCHY, is directed to a process for removing deleterious components, for example, nitrogen-containing substances, from a fluid stream wherein the feedstream containing the deleterious components is contacted with a sorbent while in the vapor phase which is capable of selectively removing the deleterious component as compared to the remaining components contained within the feedstream and then, while still maintaining the feedstream in the vapor phase, subjecting the feedstream effluent, now having a reduced concentration of the deleterious component, to the step of the processing operation which is sensitive to the deleterious component, which step is carried out in the vapor phase at conditions suitable for such step. The ZARCHY patent emphasizes that for purposes of his invention, the hydrocarbon feed which may contain sulfide and/or ammonia is maintained in the vapor phase as it is passed through the adsorption zone at temperatures which are well above the dew point of the feedstream, generally in the range of about 250° F. to about 600° F.

U.S. Pat. No. 4,831,207, O'KEEFE et al., is directed to a process similar to the one disclosed by ZARCHY, which utilizes two adsorption zones to provide for continuity of the adsorption step which are switched or cycled in service at intervals that would preclude breakthrough of the adsorbed deleterious component. A disclosed advantage is that the fluid feedstream containing one or more of the deleterious components, such as nitrogen-containing substances, can continuously flow through an adsorption zone, the effluent from which can flow continuously to at least the sensitive step of the process, and at least a portion thereof can be passed continuously to a desorption zone. At an appropriate point in time, i.e., when the adsorption zone is substantially laden with the deleterious component and before there is any breakthrough, the adsorption zone is switched to become a desorption zone, and the desorption zone is then switched to become an adsorption zone in conjunction with the proper switching of the feedstream flow path.

Notwithstanding attempts to improve the production of isobutene and MTBE, a problem associated with conventional processes for the production of MTBE is that the catalyst material used in the catalyst reaction processes has a tendency to deactivate in an unacceptably short period of time.

SUMMARY OF THE INVENTION

The present invention is based on the discovery that nitrogenous components in a feedstream, such as nitrogen containing materials, e.g., nitriles, i.e., acetonitrile ($CH_3CN$); amines, including alkylamines ($CH_3NH_2$), diethanolamine (DEA), monoethanolamine (MEA); amides, such as dimethylformamide (DMF); pyrrolidines, e.g., methylpyrrolidine (NMP); and ammonia ($NH_3$), if present in hydrocarbon streams, react with acidic sites on catalyst material so as to result in the neutralization of these sites with the concomitant loss of catalyst activity.

An object of the present invention, therefore, is the provision of methods for conducting catalytic reaction processes wherein the components of the hydrocarbon stream are catalytically reacted under conditions which favor forming resultant products, i.e., ethers, such as alkyl tertiary alkyl ethers having a normal boiling point in the range of 130° F.-200° F., and particularly MTBE, while inhibiting the reaction of nitrogenous components, such as nitrogen containing materials, e.g., nitriles, i.e., acetonitrile; amines, including alkylamines, diethanolamine, monoethanolamine; amides, such as dimethylformamide; pyrrolidines, e.g., methylpyrrolidine; and ammonia which may be present in the hydrocarbon stream, with the catalyst material whereby the deactivation of the catalyst material due to the reaction of such nitrogenous components with the catalytic material is substantially reduced or avoided. Although some of these nitrogenous substances may be naturally present in hydrocarbon streams, the hydrocarbon stream typically becomes contaminated with such nitrogenous substances as a result of being subjected to upstream extraction processes using such nitrogenous substances, for example, as solvents which become entrained in the hydrocarbon stream leading to the downstream catalytic reactors.

In general, the present invention is directed to any catalytic reaction process, but preferably to catalytic distillation reaction processes, performed in a manner which minimizes or substantially avoids the reaction of nitrogenous components of a hydrocarbon feedstream, containing saturated and/or unsaturated hydrocarbons, and particularly $C_4$ hydrocarbons, and particularly unsaturated $C_4$ hydrocarbons, such as olefins, and the catalytic material, which has been discovered to be responsible for deactivation of acidic catalysts used in the catalytic distillation reaction zone.

In accordance with the present invention, the nitrogenous substances present in the hydrocarbon stream may be removed by subjecting the streams to an adsorption treatment before introducing the stream into the catalytic reaction zone. Preferably the adsorption of the nitrogenous components is performed in a cyclic operation involving the use of two adsorption columns.

The present invention relates to a process for purifying a hydrocarbon feedstock which contains at least one nitrogenous contaminant selected from the group consisting of nitrogen-containing compounds, wherein the nitrogen-containing compounds are selected from the group consisting of nitriles, i.e., acetonitrile ($CH_3CN$); amines, including alkylamines ($CH_3NH_2$), diethanolamine (DEA), monoethanolamine (MEA); amides, such as dimethylformamide (DMF); pyrrolidines, e.g., methylpyrrolidine (NMP); ammonia ($NH_3$) and mixtures thereof.

The process involves the steps of contacting feedstreams of the hydrocarbon feedstock, and preferably $C_4$ unsaturated hydrocarbon streams, containing such nitrogenous contaminants with an adsorbent selected from the group consisting of zeolites, aluminas, clays under conditions suitable for the adsorption of at least one contaminant by the zeolite to produce a contaminant-loaded zeolite.

Although zeolites are the most preferred adsorbents for purposes of the present invention, other adsorbent materials which are no more acidic than zeolite may also be used. The preferred zeolites, however, are selected from the group consisting of zeolite X, and zeolite Y (which also may be referred to as faujasites when naturally occurring), zeolite L, zeolite beta and mordenite.

The zeolite preferably has a pore size of between about 5 to about 11 Angstroms, and may be substantially in the form of crushed or beaded particles.

In a particularly preferred embodiment, a cation type X zeolite is more preferred, with NaX zeolite being most preferred.

In the process according to the present invention, the feedstream, preferably in the liquid state, may be contacted with the zeolite at a weight hourly space velocity of from about 0.5 to about 10, with a weight hourly space velocity of from about 1 to about 8 being preferred, about 1 to about 3 being more preferred, and about 1 to about 2 being most preferred.

The operating temperature used for conducting the process according to the present invention may range from about 0° C. to about 200° C., preferably within the range of about ambient to about 100° C., with a range of from about 20° C. to about 40° C. being more preferred, and a range of from about 25° C. to about 35° C. being most preferred. In general, however, temperatures and pressures sufficient to maintain the feedstock in the liquid state are preferred for use in accordance with the present invention.

While it is to be understood that the process according to the present invention is suitable for practice on a variety of hydrocarbon feedstocks, which will contain an extremely varied and diverse assortment of contaminants, the adsorption process of the present invention has been discovered to be a particularly preferred removal technique where the hydrocarbon feedstream contains nitrogenous contaminants which may be present in the feedstream in an amount up to about 2000 ppm, but typically within the range of about 1-300 ppm, more typically at a concentration within the range of about 1 ppm to about 100 ppm, and most typically at a concentration of from 5 ppm-50 ppm.

In the preferred embodiment of the present invention which is directed generally to the treatment of $C_4$ unsaturated hydrocarbon streams, for purposes of producing methyl tertiary butyl ether (MTBE), the preferred components of the hydrocarbon feed comprise isobutylene and methanol, and preferably comprise isobutylene, butenes, $C_4$ saturated hydrocarbons, $C_3$ hydrocarbons and $C_5$ hydrocarbons. The hydrocarbon streams suitable for purposes of the present invention have a boiling point within the range of about 10° F. -47° F. The hydrocarbon streams may also comprise water and sulfur contaminants, such as dialkyl sulfides, e.g., dimethyl sulfide (DMS). The hydrocarbon stream most preferred in the preparation of methyl-t-butylether (MTBE) comprises about 25% of a mixture of isobutylene and butene-1, about 20% butene-2, about 50% $C_4$ saturated hydrocarbons, and about 5%-10% $C_3$ hydrocarbons and $C_5$ hydrocarbons.

The adsorption of the present invention has been discovered to be the preferred removal process for treating hydrocarbon streams, which are to be subjected to a catalytic reaction processes, which contain sulfur contaminants and specifically dialkyl sulfides, i.e., dimethyl sulfide, wherein the nitrogenous contaminants, such as nitriles, and most preferably acetonitriles, are present in amounts less than about 2000 ppm, and more preferably less than about 300 ppm, but most preferably where acetonitrile is present within the range of about 1 ppm to about 100 ppm, and more preferably within the range of about 5 ppm to about 50 ppm.

BRIEF DESCRIPTION OF THE DRAWING

The Figures annexed hereto are flow diagrams showing catalytic distillation processes in accordance with the present invention.

DETAILED DESCRIPTION

Figure 1:
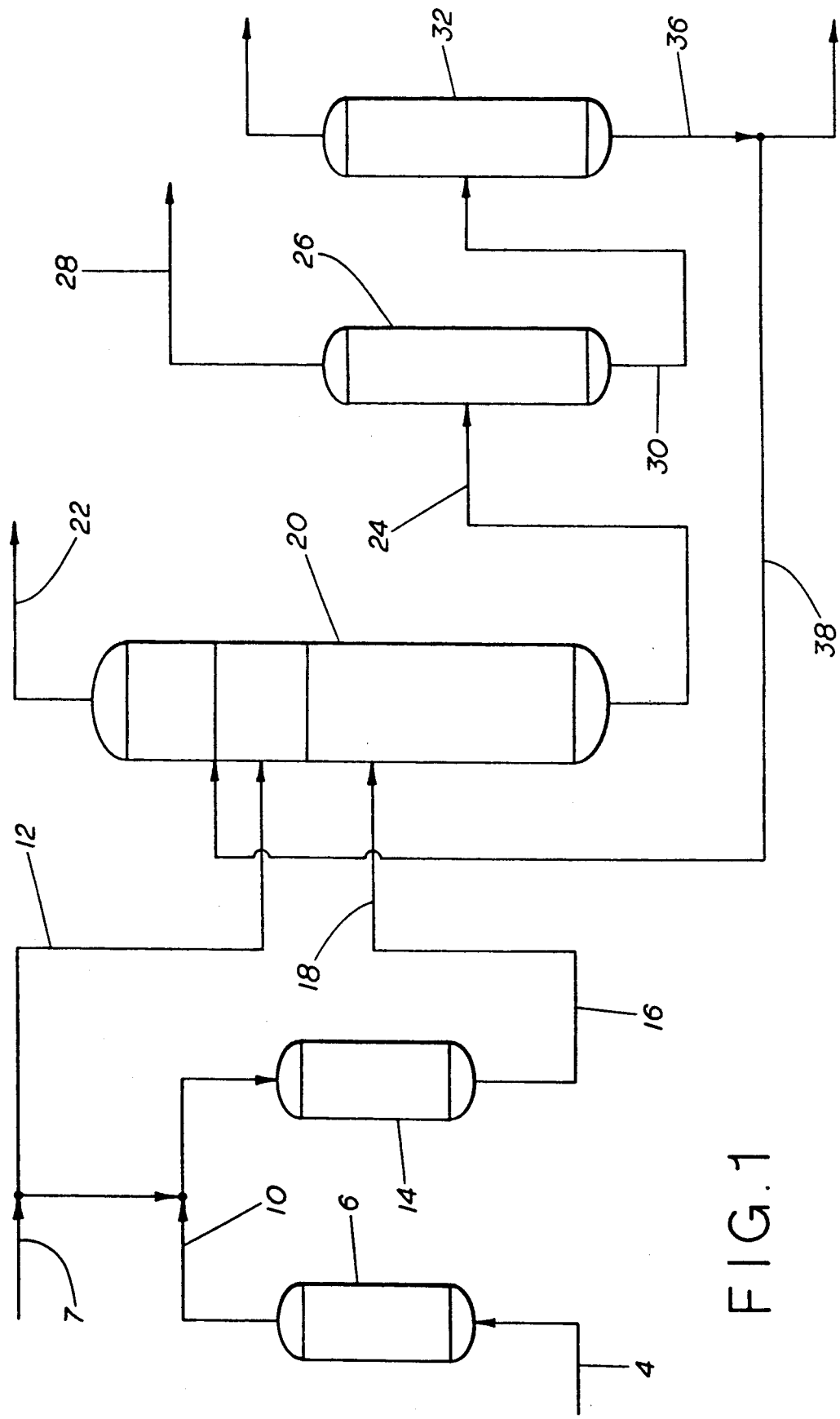
FIG. 1 is a flow diagram of a catalytic distillation process, wherein an adsorption column is installed prior to the mixing point of the hydrocarbon stream feed and the methanol streams.

The present invention is based on the discovery that typical hydrocarbon streams which are subjected to catalytic reaction processes, e.g., in the producing of ethers, such as streams containing $C_4$ hydrocarbons, i.e., unsaturated hydrocarbons, which are used in the production of alkyl tertiary alkyl ethers, and particularly such ethers having a normal boiling point within the range of 130° F.–200° F., and most notably MTBE, contain sulfur contaminants, and specifically dialkyl sulfides, i.e., dimethyl sulfide, in addition to nitrogenous contaminants, such as nitrogen-containing substances or materials which react in the presence of the acidic sites on the catalyst material so as to result in the neutralization of these sites with the concomitant loss of catalyst activity. This has been found to be particularly the case for the production of MTBE by catalytic distillation reaction processes.

Thus, the present invention relates to performing catalytic reactions in a manner which minimizes or substantially avoids reaction of nitrogenous contaminants, and particularly nitrogen-containing materials which may be present in the hydrocarbon stream when fed or introduced into the catalytic reaction zone, i.e., the lead synthesis reactor and the catalytic distillation column, even though the hydrocarbon stream may have previously been subjected to procedures in an attempt to remove contaminants, such as sulfur and nitrogen contaminants, therefrom. Accordingly, the present invention is directed to any catalytic reaction process, but preferably to catalytic distillation reaction processes, which are performed in a manner which minimizes or substantially avoids the reaction of nitrogenous contaminants, as well as dialkyl sulfides such as dimethyl sulfide, in the presence of the catalytic material which has been discovered to contribute to deactivation of acidic catalysts used in the catalytic distillation reaction zone.

In general, therefore, the present invention is directed to any process whereby a reaction of dimethyl sulfide, nitrogenous contaminants, and catalyst material, is minimized or substantially avoided.

One embodiment of the present invention relates to catalytic reaction processes of hydrocarbon streams and particularly catalytic reactions of $C_4$ hydrocarbon streams, e.g., isoolefins, such as isobutene, containing dimethyl sulfide and nitrogen-containing materials, over an acid catalyst, such as an acid resin catalyst. In this embodiment, the deactivation of the catalyst material used in such catalytic reaction processes is minimized or substantially eliminated by removing, and preferably substantially alcohols, $C_5$ alcohols and ethanol in addition to methanol.

A critical parameter in catalytic reactions, such as the manufacture of MTBE, is the maintenance of high catalytic activity. In the synthesis of MTBE, as practiced in the art, however, catalyst deactivation has been shown to occur by different mechanisms in different areas of the process. For example, as disclosed in commonly-owned application U.S. application Ser. No. 07/274,557, it is recognized that, in the fixed bed or tubular reactor wherein an acidic resin such as Amberlyst 15 (trademark) is employed to catalyze the formation of MTBE from isobutene and methanol, deactivation of the catalyst occurs over time if the catalyst is exposed to cationic or strongly basic material, such as metals, nitrogen compounds and the like. In order to drive the reaction of methanol and isobutene to MTBE to completion, therefore, it has been proposed to use the same acidic resin catalyst downstream of a first stage reactor, thereby permitting more complete utilization of the isobutene in the feed.

The solution to avoid catalyst deactivation proposed in U.S. application Ser. No. 07/274,557, was based on the discovery that catalyst deactivation results from the reaction of low levels, i.e., as low as 10 ppm or lower, of dimethyl sulfide with highly acidic catalyst sites which are present primarily due to the relatively low levels of methanol, i.e., about 0.6–2 wt.%, and MTBE in the reaction zone. One alternative solution disclosed in U.S. application Ser. No. 07,274,557 is that increasing the levels of oxygenates, i.e., methanol or other alcohols as well as ethers, attenuates the acidity of the catalyst so that reaction between dimethyl sulfide and catalyst is substantially reduced without adversely affecting the reaction of choice, i.e., the reaction of alcohol and isobutene to MTBE.

Another alternative to minimize the adverse effect of dimethyl sulfide disclosed in U.S. application Ser. No. 07,274,557, is to install an adsorption column prior to the mixing point of the feed and methanol streams in a catalytic distillation procedure for the expressed purpose of removing such sulfide contaminants therefrom before exposing the catalyst to the feed.

The present invention, as disclosed and claimed herein, however, is specifically directed to removal of nitrogenous contaminants, i.e., as nitrogen-containing compounds, e.g., nitriles, such as acetonitrile, and the like as otherwise identified herein, in addition to dialkyl sulfides, such as dimethyl sulfide, from the hydrocarbon feedstream to minimize deactivation of the catalyst caused thereby.

The nitrogenous contaminants of the feedstream which are a primary concern for purposes of the present invention include members of a group consisting of ammonia, alkylamines, diakyl amine, such as diethyl amines, diethanolamine, monoethanolamine, acetonitrile, dimethylformamide and methyl-pyrrolidine, although any nitrogenous substance present in the feedstream which poses a problem for the catalyst in the downstream catalytic reactions would also be subject to treatment in accordance with the present invention. The previously mentioned nitrogenous contaminants with which the present invention is primarily concerned, however, are normally those which may contaminate the feedstream as a result of upstream processing, for example, in upstream extraction units which may leak nitrogenous solvents which contaminate the feedstream.

As disclosed in U.S. application Ser. No. 07,274,557, unless special steps are taken to remove dialkyl sulfides, such as dimethyl sulfide, from such feedstreams, the feedstream must also be treated to remove or otherwise minimize the deleterious effects of the dimethyl sulfide which are present in the feedstream so as to prevent deactivation of the catalyst used in the downstream catalytic reaction zones. Although nitrogenous contaminants may not always be present in the feedstream which is to ultimately be subjected to such catalytic reactions, depending upon the upstream processing to which the hydrocarbon feedstream has been subjected or the source of the hydrocarbon feedstream, it has been observed that the hydrocarbon feedstream will substantially always include an amount of dimethyl sulfide which must be removed prior to catalytic reaction in order to minimize the deactivation of the catalyst used in the downstream catalytic reactions.

Thus, the present invention is based on the discovery of an adsorbent material which effectively removes dimethyl sulfide present in the feedstream as well as nitrogenous substances which may also be present in the feedstream.

Adsorbent materials which have been discovered to be suitable for this purpose are adsorbent materials which are substantially devoid of protons as a cation, i.e., which have relatively low acidity, such as zeolite, which preferably are selected from the group consisting of zeolite X and zeolite Y (which may also be referred to as faujasites) zeolite beta and mordenite. The zeolite used for purposes of the present invention preferably has a pore size of between about 5 to about 11 Angstrom units and may be substantially in the form of crushed or beaded particles. A more preferred zeolite includes a cation X zeolite, with NaX zeolite being most preferred.

The acidity of the adsorbent material used for purposes of the present invention is critical inasmuch as hydrocarbon feedstreams which may be processed in accordance with the present invention include saturated as well as unsaturated hydrocarbons. This being the case, the acidity of the adsorbent is of a concern because it has been discovered that if an adsorbent material having too high acidity is used, the acidity of the adsorbent could promote undesirable reactions of the unsaturated hydrocarbons, for example, polymerization, isomerization, and the like. In particular, for purposes of the preferred embodiment wherein the present invention finds particularly utility, there is a concern for minimizing the reaction of isobutylene prior to its reaction with alcohol in the preparation of MTBE. Thus, it has been discovered that zeolites are preferred catalysts for purposes of the present invention with this consideration in mind.

Another critical aspect of the adsorbent material used for purposes of the present invention is that the adsorbent material must not only be effective for purposes of adsorbing the nitrogenous substances, which are of primary concern for purposes of the present invention, but also an adsorbent material which is also effective for removing sulfides, and particularly dialkyl sulfides, such as dimethyl sulfide, from the feedstream. As previously indicated, although the feedstream may not always contain nitrogenous contaminants, depending on how the feedstream was previously treated in upstream processing, unless special steps are taken to remove dimethyl sulfide from the feedstream, as disclosed in U.S. application Ser. No. 07,274,557, the dimethyl sulfide which is present in the feedstream must also be removed, or the feedstream must be otherwise treated in order to prevent deactivation of the catalyst used in the downstream catalytic reaction zones, i.e., the lead synthesis reactor and the catalytic distillation column.

Therefore, the present invention is directed to the removal of contaminants, i.e., nitrogenous substances as well as dimethyl sulfide, which would be harmful to the downstream catalytic reaction zones, but not to the detriment of the removal of dimethyl sulfide which is substantially always present in the feedstream to be subjected to such reactions.

Related to this, it has been unexpectedly discovered that NaX zeolite is a most preferred adsorbent material for this purpose. In this regard, NaX zeolite has a specified capacity for the adsorption of sulfides, for example, of about 3%. A common concern, therefore, is the effect that the presence of other contaminants, for example, nitrogenous containing contaminants, such as nitriles, may have if present in the feedstream undergoing the adsorption treatment. In accordance with the present invention, therefore, it has been discovered that NaX zeolite also has an adsorption capacity of about 15% for nitriles; thus, there is a similar concern as to whether the capacity of the adsorbent material for nitriles, such as acetonitriles, would be adversely affected by the presence of sulfur components, i.e., dialkyl sulfides such as dimethyl sulfide, which, as indicated above, is substantially always present.

As previously indicated, the concern for an adsorbent material which effectively removes nitrogenous contaminants, as well as dimethyl sulfide, is of a primary concern for purposes of the present invention inasmuch as the dimethyl sulfide has been discovered to substantially always be present in the feedstream unless extraordinary steps are taken to effect their removal; and that this is true regardless of whether the feedstream has been subjected to conventional sulfur-removal techniques.

In this regard, the feedstreams to be subjected to subsequent catalytic reactions normally contain dimethyl sulfide in a concentration of up to about 50 ppm. When the nitrogenous contaminants are present in such a feedstream, the nitrogenous contaminants may be present at a concentration up to about 1000 ppm, but more often within the range of up to about 300 ppm, and most often within the range of about 5 ppm-50 ppm. In such amounts, for example, where the amounts of acetonitrile and dimethyl sulfide are substantially equal, NaX zeolite has been found to be most preferred for purposes of effectively removing both the nitrogenous contaminants, as well as the dimethyl sulfide, from the feedstream. As indicated above, however, normally the nitrogenous contaminants are present in the feedstream in an amount greater than the dimethyl sulfide. Although if the level of nitrogenous contaminants is substantially greater than the level of dimethyl sulfide in the feedstream, i.e., in amounts greater than about 300 ppm-1000 ppm, the presence of such high amounts of nitrogenous contaminants may adversely affect the performance of the adsorbent material. Accordingly, it has been discovered that for purposes of the present invention the ratio of nitrogenous substances to dimethyl sulfide may be present within the range of 1:1 to about 20:1 before the performance of, for example, NaX zeolite, may be observed to be adversely effected.

The present invention is, therefore, based on the discovery of the fact that the presence of nitrogenous contaminants within these prescribed ranges does not adversely affect the adsorption of dimethyl sulfide by zeolite adsorbent material, such as NaX zeolite. As previously indicated, this is a particularly important discovery inasmuch as the zeolites used in accordance with the present invention, and particularly NaX zeolite, have been discovered to have a high capacity for adsorbing acetonitriles. Such zeolite have also been discovered to adsorb acetonitrile to substantially complete capacity for acetonitriles without having its capacity for adsorbing dimethyl sulfide, which is substantially always present in the feedstream and must also be removed, adversely affected, i.e., this acetonitrile capacity does not affect the zeolite capacity for adsorbing dimethyl sulfide.

Therefore, the present invention is based on the new and unobvious discovery that zeolites, and preferably NaX zeolite, are not only an effective adsorbent material for nitrogen-containing substances, but also effectively adsorb dimethyl sulfide, which has been discovered to be a particularly difficult sulfur contaminant to remove from hydrocarbon streams and which is not always removed by conventional sulfur removing techniques that, for example, would be effective to remove other sulfur contaminants, such as mercaptans.

EXAMPLES

The following examples are given to illustrate the advantages of the present invention.

EXAMPLE I

Laboratory static tests were carried out to determine the ability of NaX to adsorb nitrogenous compounds. The results showed that a feed containing dimethylformamide (DMF) at the 290 ppm level can be lowered to 13 ppm. With monoethannamine a feed level of 70 ppm changed to 9 ppm.

A dynamic test was carried out using a 5 cc charge of NaX at 35° C. The feed contained 10% isobutylene, 90% n-heptane and 195 ppm each of dimethylsulfide/acetonitrile. The sieve capacity for sulfur at DMS breakthrough was 2.96%. At that point the acetonitrile had not broken through and was at a capacity of 6.2%.

TABLE I

| Static Equilibrium Test | NaX Initial Concentration | Final Concentration |
|---|---|---|
| dimethylformamide (DMS) | 290 ppm | 13 ppm |
| monoethanolamine | 70 ppm | 9 ppm |

Dynamic Tests

The feed contained 10% isobutylene, 90% n-heptane, and 195 each of dimethylsulfide and acetonitrile. The capacity of NaX for acetonitrile is 16%.

When both acetonitrile and dimethyl sulfide are present, the DMS breaks through first. The DMS capacity at 1PPM breakthrough is about 2.5 to about 2.96% at which time no CH$_3$CN had broken through although present at a level of about 6.2%.

EXAMPLE II

Another laboratory static test was carried out to determine the ability of NaX to adsorb nitrogenous compounds. The results showed that a feed containing dimethylformamide (DMF) at the 288 ppm level can be lowered to 14 ppm; with diethanolamine, a feed level of 352 ppm changed to 56 ppm; and with ethanolamine at a feed level of 474 ppm changed to 43 ppm.

TABLE II

| | NaX | |
|---|---|---|
| Static Equilibrium | Initial Concentration | Final Concentration |
| Diethanolamine | 352 PPM | 56 PPM |
| ethanolamine | 474 PPM | 43 PPM |
| dimethylformamide | 288 PPM | 14 PPM |

Dynamic Tests

Another dynamic test was carried out using a 5cc charge of NaX at 35° C. The feed contained 10% isobutylene, 90% n-heptane and 198 ppm of dimethylsulfide and 145 ppm of acetonitrile. The sieve capacity for sulfur at DMS breakthrough was 2.5-2.96%. At that point the acetonitrile had not broken through. Capacity of NaX for acetonitrile is 16%.

EXAMPLE III

The following example shows that NaX zeolite adsorbs various nitrogen-containing compounds, preferably other than nitriles, as well as examples which show the effectiveness of NaX zeolite as an adsorbent for nitrogen-compounds alone and in combination with dimethyl sulfide in a feedstream.

TABLE IIIA

NaX 10 × 14 MESH CRUSHED TO 40 × 60 MESH DRIED AT 170° C./48 HOURS

| Run | Feed Rate ml/min | DMS ppm | CH$_3$CN ppm | Temp. °C. % | DMS CAPACITY % |
|---|---|---|---|---|---|
| 1 | 0.446 | 203.4 | 200 | 35 | 2.47 |
| 2 | 0.416 | 178.3 | 200 | 35 | 2.03 |
| 3 | 0.391 | 183 | 200 | 35 | 3.04 |
| 4 | 0.45 | 181.6 | 193.8 | 35 | 3.62 |
| 5 | 0.417 | 181 | 3621 | 35 | — |
| 6 | .407 | 186 | 1800 | 35 | 1.28 |

If acetonitrile concentration is increased to 0.18% (1800 ppm) while DMS concentration is kept at 190 ppm then the DMS capacity drops to 1.3% at breakthrough.

TABLE IIIB

CRUSHED TO 40 · 60 MESH NaX DRIED AT 170° C./48 HOURS

| Run | CH$_3$CN Fd ppm | DMS Fd ppm | Feed Rate ml/min | Temp. °C. | CH$_3$CN Capacity % | DMS Capacity % |
|---|---|---|---|---|---|---|
| 1 | 198 | 194.6 | 0.41 | 35 | 6.22* | 2.96 |
| 2 | 211/193 | — | .42/.65 | 35 | 14.05 | — |
| 3 | 193.3 | — | 0.80 | 35 | 16.06 | — |

*at DMS breakthrough

When both acetonitrile (198 ppm) and dimethyl (145 ppm) sulfide are present the DMS breaks through first. The DMS capacity at IPPM breakthrough is 2.5-2.96%. At this time no CH$_3$CN has broken through.

For purposes of the present invention, the catalyst material used in the downstream reaction zone may be any material appropriate for the downstream reaction, but is preferably an acid catalyst, such as catalytic metals and their oxides or halides suitable for a multitude of catalytic reactions and particularly heterogeneous with the reaction or other fluids in the system. The term "catalyst" or "catalytic material", therefore, as used herein includes any solid material which is recognized for the reaction under consideration as performing as a catalyst.

For example, where the present invention is practiced in a catalytic distillation process, the catalytic material may be in a form which permits its incorporation into a distillation tower, such as a fixed bed, but may also be in a form which serves as a distillation packing, for example, rings, saddles, balls, irregular pieces, sheets, tubes, spirals, packed in bags, plated on grills or screens, and reticulated polymer foams.

Catalysts which have been found to be suitable for use in such catalytic reactions include cation exchange resins. Preferred catalysts for this purpose, however, are acid catalysts, such as acidic resin catalysts. A more preferred catalyst for this purpose is a macroreticular sulfonic acid cation exchange resin, selected from the group consisting of Amberlyst 15 (trademark), Lewatit SPC 18 BG, Dowex M-31 and Dowex DR-2040, with Dowex DR-2040 being most preferred.

Referring now the Figures, a schematic system is shown, which can be used to produce MTBE.

In FIG. 1, a hydrocarbon stream containing a stoichiometric amount of methanol based on isobutylene is introduced together with an isobutylene containing stream to a lead synthesis, or guard bed, reactor 14. For purposes of the present invention, however, the nitrogenous contaminants in the feedstream 4 may be removed by installing an adsorption column 6 prior to the mixing point of the hydrocarbon feed 10 and methanol 7 streams. The removal of nitrogenous contaminants has been discovered to be most effective for a methanol-free feedstream. Although not shown, in practice, the removal is preferably accomplished with a cyclic operation involving the use of two adsorption columns so that while one column is adsorbing the sulfides or the nitrogenous substances, the other column is being regenerated to recover the capacity. The preferred process according to the present invention, therefore, comprises two fixed beds of solid adsorbent being operated in cyclic fashion, so that one bed is undergoing adsorption while the other bed is being desorbed. Before the process is initiated, the beds are preferably blanketed with hot nitrogen to create a dry oxygen-free environment. This prevents oxygen from being introduced into the hydrocarbon stream; otherwise, oxidative degradation of the feed hydrocarbon components could occur, resulting in formation of undesirable side products.

When the bed undergoing adsorption reaches the end of its cycle, as measured by a breakthrough value for the contaminant, i.e., nitrile or sulfide in the adsorption effluent, the beds are switched. The switching may be accomplished using a programmable controller and remote-operated valves. A typical adsorption cycle will last from about 4 hours to about 75 hours, but can vary considerably depending on variables such as feed rate, the concentration of contaminants, i.e., nitriles or sulfides in the feed, the age of the solid adsorbent and the amount of adsorbent used. The lead synthesis reactor or guard bed reactor 14 is provided with an acidic resin catalyst, such as Amberlyst-15 (trademark), Dowex DR-2040, Lewatit SPC 18 BG, or Dowex M-31, and is heated to an appropriate temperature. The effluent or product stream 16 leaving the reactor is composed of MTBE, unreacted hydrocarbons, and methanol (MeOH). The resultant product stream is the feedstream 18 which is then fed to a distillation column 20. The vaporized overhead 22 is composed of raffinate depleted in olefins branched at the point of unsaturation (sometimes referred to as tertiary olefins) which is passed through methanol removal and final clean-up procedures.

Consistent with the process disclosed in U.S. application Ser. No. 07,274,557, a stream 12 of methanol may be introduced into the catalytic distillation reaction zone. The catalyst in the catalytic distillation reaction zone may also be Amberlyst 15 or equivalent, but is preferably Dowex DR-2040. The effluent is then passed to a product topping tower 26, wherein $C_5$ hydrocarbons are removed for separate processing. The resultant effluent stream 30 is then passed to product tailing tower wherein MTBE is removed as overhead product. The effluent 36 from tailing tower contains various components including oxygenates, such as TAME, which are recycled through conduit 38 to supply oxygenate to catalyst reaction zone.

Notwithstanding the foregoing to preferred embodiment, catalytic reaction processes which are suitable to being practiced in accordance with the present invention may be a catalytic distillation process performed in a conventional manner, such as that which is disclosed by any of the previously discussed U.S. patents in the name of SMITH, Jr.; the disclosures of which are hereby specifically incorporated by reference thereto.

Figure 2:
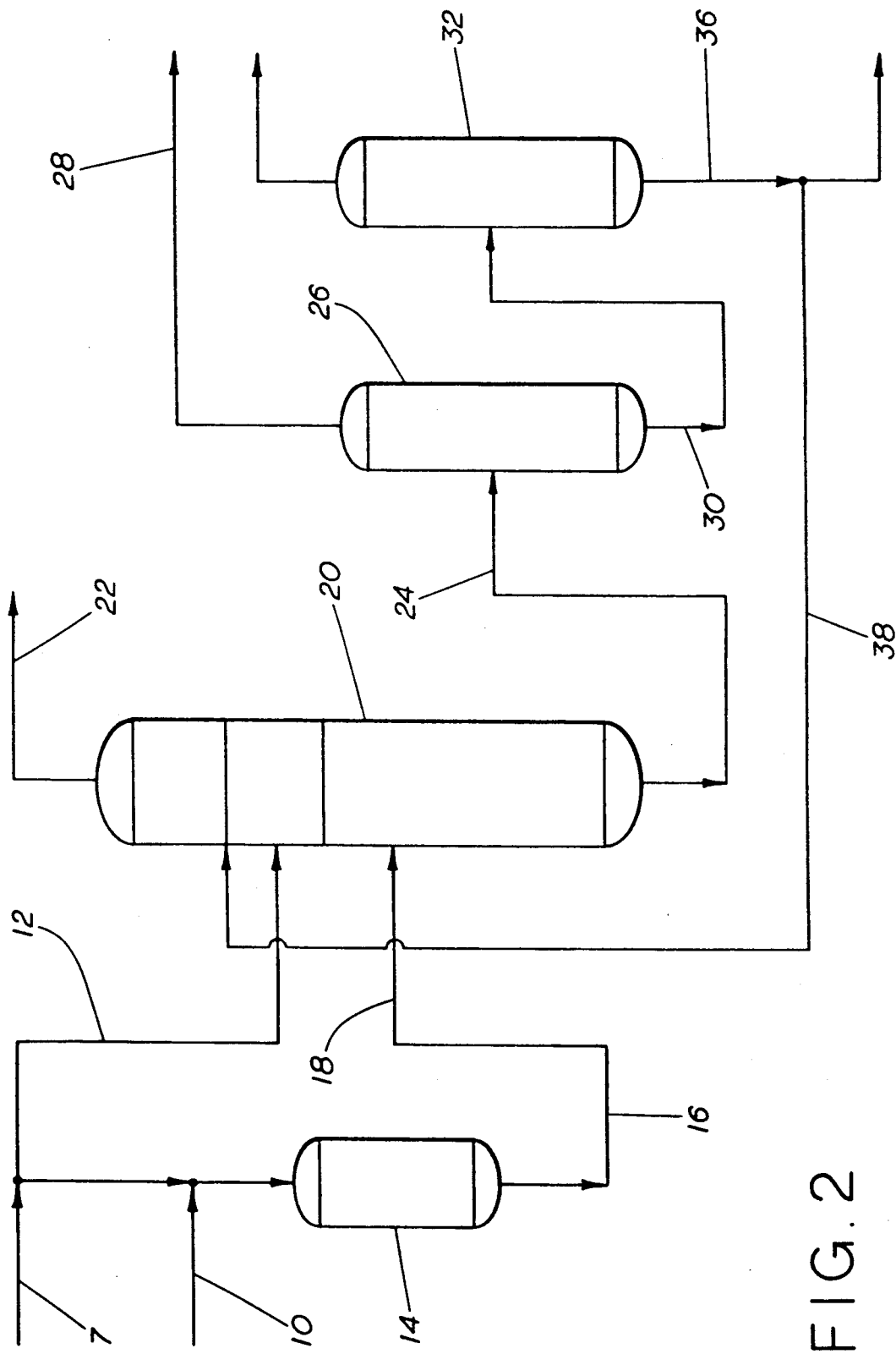
FIG. 2 is a flow diagram of a conventional catalytic distillation process which is not equipped with an adsorption column in accordance with the present invention.

Referring to FIG. 2, a feedstream 10 containing 13 wt.% isobutylene, 30 wt.% isobutane, 14 wt.% butene-1, 13 wt.% n-butane, 18% 2-butenes, 0.5 wt.% butadiene, 6% isopentane, approximately 5 wt.% other $C_5$ hydrocarbons (including paraffins, olefins, and diolefins), 200 wt. ppm methyl and ethyl thiol and 10 wt. ppm dimethyl sulfide are combined with a methanol stream 7 in the weight ratio of methanol in stream 7 to isobutylene in stream 10 of 0.75:1.0. This combined stream is heated to 130° F. to 170° F. and introduced to a lead synthesis reactor which contains acidic ion exchange resin catalyst such as Amberlyst 15 (trademark) in a quantity which provides for a weight space velocity of 3.5 W/H/W to 4.0 W/H/W.

In passing through the lead synthesis reactor 14, approximately 85 wt.% of the isobutylene in the feedstream is converted to MTBE. In contrast to the present invention described above wherein the hydrocarbon stream is exposed to an adsorption treatment before being subjected to catalytic reaction to remove nitrogenous contaminants, in this reactor, strongly basic compounds and metallic compounds contained in the hydrocarbon or methanol feed react with acidic catalyst. Although this may remove the contaminants from the feed, so as to minimize their adverse effect on the catalyst in the downstream catalytic distillation tower 20, in so reacting with the catalyst, however, these basic compounds reduce the number of acidic sites on the catalyst, and over time result in its deactivation.

The hydrocarbon stream 16, which exits reactor 14, contains 17 wt.% MTBE, about 2 wt.% isobutylene and all the remainder of unreacted hydrocarbon and methanol. This stream is fed to a catalytic distillation tower 20. The overhead from this column containing only 0.5 wt.% isobutylene in hydrocarbons is passed through methanol removal and sent to other processing.

In accordance with the present invention, therefore, a procedure has been developed to minimize or substantially eliminate the deleterious effects which would otherwise be caused by the presence of nitrogenous contaminants in the catalytic reaction zone. This is accomplished by adsorbing the nitrogenous contaminants, and particularly nitrogen-containing materials and compounds, such as nitriles and amines, from the hydrocarbon feedstream before the feedstream contacts the catalyst in either the lead synthesis reactor 14 or the catalytic distillation tower 20.

EXAMPLE IV

The following test was conducted to evidence that the previously identified adsorbents are effective to remove nitrogen-containing materials from an ether synthesis hydrocarbon stream.

The experiments were carried out with a laboratory-scale, continuous-flow tubular reactor. A 5 cc charge of sodium-X zeolite was placed in a stainless steel column and held in place by porous metal plugs. The tube was kept at ambient temperature. The single liquid feed was introduced by an HPLC pump controlling the liquid flow to yield a Liquid Hourly Space Velocity of 3.6. The temperature was maintained at 22° C. and back pressure at the exit of the tube was kept at 200 psig. The feed was a synthetic blend of 10% isobutylene, 90% n-heptane and 200 ppm acetonitrile. The acetonitrile concentration in the column effluent was less than the GC detectable limit of 5 ppm before the acetonitrile loading on the NaX zeolite reached a level of 12.8 wt.%.

Notwithstanding the foregoing detailed discussion of preferred embodiments, in general it can be said that the present invention may be used in connection with any reaction of a hydrocarbon stream over an acid catalyst, such as Amberlyst 15 or Dowex DR-2040. Included among the catalytic reactions to which the discoveries of the present invention are believed to be suitable are catalytic isomerization, esterification, dimerization, cracking and distillation processes, although all other types of reactions are contemplated within the scope of the invention process, for example, chlorination, hydration, dehydro-halogenation, alkylation, polymerization and the like.

It is also believed that in general isomerization reactions over acidic ion exchange resin catalysts can be improved and deactivation of the catalyst minimized by removing such nitrogenous contaminants from the hydrocarbon stream. Accordingly, the principles of the present invention may be applied to the isomerization of numerous hydrocarbon feed compositions, such as feedstreams containing a mixture of saturated hydrocarbons, other straight chain and branched olefins, and small amounts of certain diolefins. One example of such a feed is the naphtha fraction from a refinery catalytic cracking unit.

Although in the past it has been suggested to include alcohols and water at this stage of catalytic isomerization reactor to provide the necessary environment to render the catalyst operable, it has been found that alcohols tend to react with the isoolefins to form ethers, thereby resulting in a product loss. Moreover, the presence of water causes solubility problems and also tends to react with the isoolefins to form alcohol; thus, water is not a particularly desirable solvent. Water also tends to deactivate the catalyst. It has been proposed to include ether with isoolefins to provide the necessary environment for resin catalyst operability, with tertiary amyl methyl ether (TAME) and methyl tertiary butyl ether (MTBE) being preferred, and TAME being most preferred for this purpose.

Although the invention has been described with reference to particular means, materials and embodiments, from the foregoing description, one skilled in the art can easily ascertain the essential characteristics of the present invention; and various changes and modifications may be made to various usages and conditions, without departing from the spirit and scope of the invention as described in the claims that follow.

What is claimed is:

1. A method of producing an ether and treating a stream comprising nitrogen-containing substances, said process comprising:
   a) passing a stream comprising hydrocarbons and nitrogen-containing substances over a zeolite selected from the group consisting of zeolite X, zeolite Y, zeolite L, zeolite Beta, and Mordenite under conditions effective to permit said zeolite to adsorb said nitrogen-containing substances to result in a substantially purified stream comprising hydrocarbons which is substantially devoid of said nitrogen-containing substances, prior to
   b) supplying a feedstream comprising said substantially purified stream comprising hydrocarbons, olefins and alcohols to a reactor, and
   c) reacting said feedstream in the presence of an acid cation exchange resin catalyst under conditions which favor ether formation.

2. The method as defined by claim 1, wherein said nitrogen-containing materials are selected from the group consisting of a nitrile, an amine, an amide, and ammonia and mixtures of two or more of nitriles, amines, amides, and ammonia.

3. The method as defined by claims 2, wherein said nitrogen-containing materials is a nitrile.

4. The method as defined by claim 3, wherein said nitrile is an acetonitrile.

5. The method as defined by claim 2, wherein less than about 2000 ppm of said nitrogen-containing materials are present in said stream.

6. The method as defined by claim 5, wherein less than about 300 ppm of said nitrogen-containing materials are present in said stream.

7. The method as defined by claim 6, wherein said nitrogen-containing materials are present in said stream in an amount within the range of about 5 ppm to about 50 ppm.

8. The method as defined by claim 2, wherein said stream further comprises dialkyl sulfides.

9. The method as defined by claim 8, wherein said dialkyl sulfides are initially present in said hydrocarbon stream in an amount within the range of up to about 200 ppm.

10. The method as defined by claim 9, wherein said nitrogen-containing substances and said dialkyl-sulfides are present in a ratio within the range of about 1:1 to about 20:1.

11. The method as defined by claim 8, wherein said zeolite is a zeolite X.

12. The method as defined by claim 11, wherein said zeolite X is a sodium-X zeolite.

* * * * *